(12) United States Patent
Mallory

(10) Patent No.: US 6,579,432 B2
(45) Date of Patent: Jun. 17, 2003

(54) PROTECTION OF GAS COMMUNICATION IN AN ELECTROCHEMICAL SENSOR

(76) Inventor: John Mallory, 3447 Ponytrail Drive, Mississauga, Ontario (CA), L4X 1V9

( * ) Notice: Subject to any disclaimer, the term of this patent is extended or adjusted under 35 U.S.C. 154(b) by 0 days.

(21) Appl. No.: 09/952,224

(22) Filed: Sep. 13, 2001

(65) Prior Publication Data

US 2002/0008023 A1 Jan. 24, 2002

Related U.S. Application Data

(63) Continuation of application No. 09/417,502, filed on Oct. 13, 1999, now abandoned.

(30) Foreign Application Priority Data

Feb. 23, 1999 (CA) .......................................... 2 262 355

(51) Int. Cl.⁷ ............................................. G01N 27/404
(52) U.S. Cl. ....................................... 204/409; 204/415
(58) Field of Search ................................ 204/409, 415, 204/431, 432

(56) References Cited

U.S. PATENT DOCUMENTS

| | | | | |
|---|---|---|---|---|
| 4,198,280 A | * | 4/1980 | Swartz | |
| 4,324,632 A | * | 4/1982 | Tantram et al. | |
| 4,948,496 A | * | 8/1990 | Chand | |
| 5,284,566 A | * | 2/1994 | Cuomo et al. | |
| 5,632,875 A | * | 5/1997 | Chapples et al. | |
| 5,830,337 A | * | 11/1998 | Xu | |
| 6,129,825 A | * | 10/2000 | Mallory et al. | |

* cited by examiner

Primary Examiner—T. Tung
(74) Attorney, Agent, or Firm—Libert & Associates; Victor E. Libert; Frederick A. Spaeth

(57) ABSTRACT

An electrochemical sensor for detection of a gas in an atmosphere containing the gas. The sensor has a housing having an electrochemical gas sensor with an electrolyte and at least two electrodes, one electrode being a gas sensing electrode. The housing has an orifice between the sensing electrode and the atmosphere for transmission of gas from the atmosphere to the sensing electrode, the orifice being protected by a hydrophobic membrane, and connected to at least two radial channels extending from the orifice. Each of the radial channels is connected to a common channel, such that gas communication from the atmosphere through the orifice to the sensing electrode is through the common channel and the radial channels, in addition to the covering membrane if the membrane is gas permeable.

15 Claims, 4 Drawing Sheets

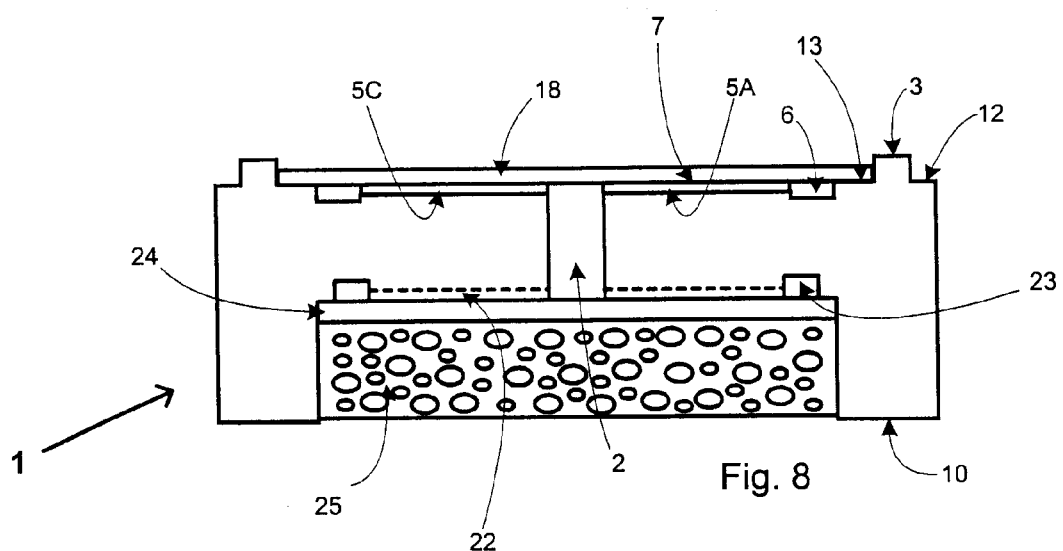

PROTECTION OF GAS COMMUNICATION IN AN ELECTROCHEMICAL SENSOR

CROSS-REFERENCE TO RELATED APPLICATION

This application is a continuation of application Ser. No. 09/417,502, filed Oct. 13, 1999, now abandoned.

FIELD OF THE INVENTION

The present invention relates to an electrochemical sensor for detection of a gas in an atmosphere containing that gas, in which the gas must pass through an orifice in the housing in order to be detected by the sensing electrode of the electrochemical sensor, and especially to the embodiments of such electrochemical sensors in which a membrane has been placed over the orifice in order to protect the orifice. In particular, the present invention relates to the provision of channels, especially a plurality of channels, for communication of the gas to or from the orifice so as to prevent blockage of the orifice by a substance or an object.

BACKGROUND TO THE INVENTION

Electrochemical sensors, including such sensors that are used in the detection of carbon monoxide, normally have a diffusion-limiting gas access hole i.e. an orifice. The gas access hole provides protection for the sensor from excessive exposure to atmospheres which contain high levels of aerosols and other contaminants. It also minimizes changes in volume of the electrolyte when the sensor is subjected to high and low humidity, as significant changes in electrolyte volume potentially lead to leaking of electrolyte as well as changes in sensor sensitivity. The gas access hole also reduces the influx of a target gas into the sensor, so that there will be fresh catalyst in the sensing electrode to ensure a long operational life for the sensor in continued and periodic detection of the target gas, and minimizes any influence of flow of air (atmosphere). The orifice is typically of a diameter of about 0.5–2 mm.

There is always a concern that an orifice of such a small diameter could become partially or completely blocked by an object. The object could be an insect or spider, which often tend to seek a small orifice for protection, for building a nest or out of curiosity. In addition, the orifice could be blocked for other reasons e.g. by condensation of water or by aerosols in the atmosphere which over a period of time could lead to blockage of the orifice.

In order to minimize the possibility of partial or complete blockage of the orifice, and consequent malfunctioning of the sensor, the orifice may be covered by a hydrophobic gas permeable membrane e.g. a membrane formed from Teflon™ fluorocarbon polymer. Examples of the use of a gas permeable membrane include the membrane disclosed in U.S. Pat. No. 4,948,496.

Even with the use of a membrane, the possibility still exists that a substantially gas-opaque deposit could form on the membrane directly above the orifice i.e. the membrane could become coated with a substance that adversely affects transmission through the membrane of the gas that is to be detected. This would retard or prevent diffusion of the gas through the membrane to the orifice and the sensing electrode, and consequently affect performance of the electrochemical gas sensor. Thus, alternate methods of protection of the orifice have been proposed, and one example is the use of a combination of a screen and a porous disc, as disclosed in U.S. Pat. No. 5,284,566, The purpose of the screen is to protect the porous disc from damage. However, such a solution to the problem of protection of the orifice in the electrochemical sensor is relatively expensive in manufacture.

SUMMARY OF THE INVENTION

A method of protection of the orifice in a simple and economical manner would be beneficial. It has now been found that gas communication in an electrochemical sensor may be protected in a manner that further reduces the possibility that the orifice will become blocked.

Accordingly, an aspect of the present invention provides an electrochemical sensor for detection of a gas in an atmosphere containing the gas, said sensor comprising a housing having an electrochemical gas sensor with an electrolyte and at least two electrodes, one such electrode being a gas sensing electrode, said housing having an orifice between the sensing electrode and the atmosphere for transmission of gas from the atmosphere to the sensing electrode, said orifice being connected to at least one radial channel extending from said orifice, such that gas communication from the atmosphere through the orifice to the sensing electrode is through said radial channel.

In a further embodiment, the orifice is connected to at least two radial channels, and more preferably to at least three and especially to at least four radial channels, optionally with each of the radial channels connecting with a common channel. The common channel may be an annular channel around the orifice.

In a preferred embodiment of the present invention, the orifice is covered to prevent direct transmission of gas into the orifice.

In a further embodiment, the orifice, radial and common channels are covered by a hydrophobic membrane.

In yet another embodiment, the orifice and optionally the radial channels are covered by a film with low gas transmission characteristics, with gas transmission to the orifice being through said common channel and radial channels.

In another embodiment, the radial channels are disposed symmetrically about the orifice.

In yet another embodiment, the radial channels and common channels are disposed on the membrane side of the orifice, the sensing electrode side of the orifice or on both the membrane and sensing electrode sides of the orifice.

BRIEF DESCRIPTION OF THE DRAWINGS

The present invention is illustrated by the embodiments of a scrubber cap for an electrochemical sensor as shown in the drawings, in which:

FIG. 8 is a schematic representation of an alternate embodiment of the scrubber cap of FIG. 5, with channels on the underside and a layer of carbon pellets.

DETAILED DESCRIPTION OF THE INVENTION

A scrubber cap is a part of the housing of an electrochemical sensor and may form a section of or be separable from the housing. The cap has an orifice therein for transmission of gas from the atmosphere to the sensing electrode of the cell, and optionally encloses carbon pellets or other materials capable of removing (scrubbing) contaminants from the gas that would adversely affect the performance of the electrochemical cell. The present invention is particularly described herein with respect to an electrochemical sensor having a scrubber cap, but it is to be understood that the electrochemical sensor could be of a different construction, not having a scrubber cap, in which case the orifice and associated channels that are described would be appropriately located in the housing of the electrochemical cell.

The present invention is particularly described herein with respect to an embodiment in which the radial channels are connected to a common channel, especially an annular common channel. It is to be understood, however, that the use of a common channel is a preferred embodiment of the invention and that one or more radial channels may be used without a common channel. In addition, the invention is illustrated with linear radial channels, but non-linear radial channels may be used. A radial channel is understood to connect to and extend away from the orifice.

Figure 1:
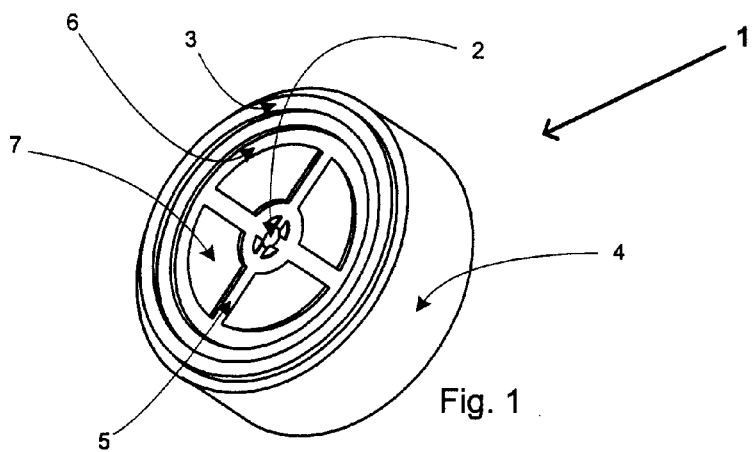
FIG. 1 is a schematic representation of a scrubber cap for an electrochemical sensor of the present invention, in a top perspective view.

FIG. 1 shows a scrubber cap for an electrochemical sensor of the invention, generally indicated by 1. Scrubber cap 1 has an orifice 2 that is centrally located in the scrubber cap. Scrubber cap 1 further has upper rim 3 on base 4, upper rim 3 being inset from the periphery of base 4 in the embodiment shown, although this is merely a preferred embodiment. Orifice 2 is connected to radial channel 5, of which four linear radial channels are shown in the embodiment of FIG. 1. Radial channels 5 extend from orifice 2 to annular channel 6. Orifice 2, radial channels 5 and annular channels 6 are all located in plate 7 of scrubber cap 1.

Figure 2:
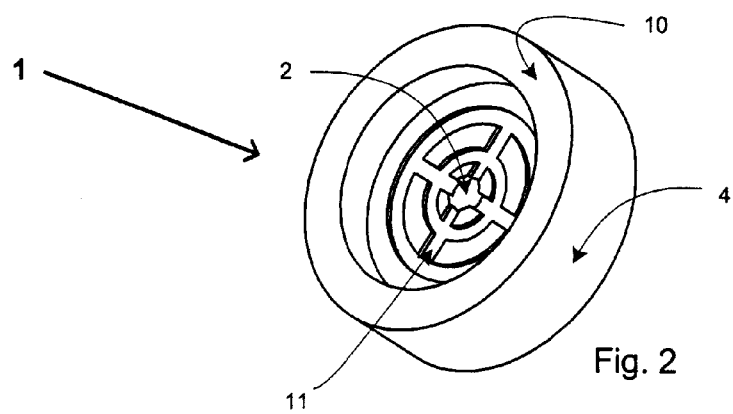
FIG. 2 is a schematic representation of the scrubber cap of FIG. 1, as viewed in a perspective from the underside.

FIG. 2 shows scrubber cap 1 viewed from the underside. Scrubber cap 1 is shown as having lower rim 10 on base 4. In the embodiment shown in FIG. 2, radial channels 11 are shown as extending from orifice 2.

FIGS. 1 and 2 show a scrubber cap having the gas communication of the present invention. The embodiment shown in FIGS. 1 and 2 has four radial channels extending from orifice 2, and terminating in an annular channel 6. It is to be understood that scrubber cap 1 could have as few as one radial channel but preferably has two or more and preferably four channels, although more channels could be used. Radial channels 5 are shown in a symmetrical arrangement around orifice 2, which is the preferred embodiment.

Each of the radial channels 5 extend from orifice 2 to annular channel 6. Annular channel 6 is conveniently shown in its preferred annular form. However, it is a common channel joining radial channels 5, and providing for gas communication to the orifice, and it may be of any convenient shape. It is also understood that the common channel does not necessarily extend fully around the scrubber cap, but could be in the form of two of more common channels, with each common channel connecting with at least one radial channel.

The invention is further described in the embodiments of FIGS. 1 and 2 as having radial channels and annular channels on both the upper surface, as seen in FIG. 1, and the lower surface, as seen in FIG. 2, of plate 7. This is a preferred embodiment, but the radial channels and annular channel could be in one of the upper surface of plate 7 or the lower surface of plate 7 or both the upper and lower surfaces of plate 7.

Figure 3:
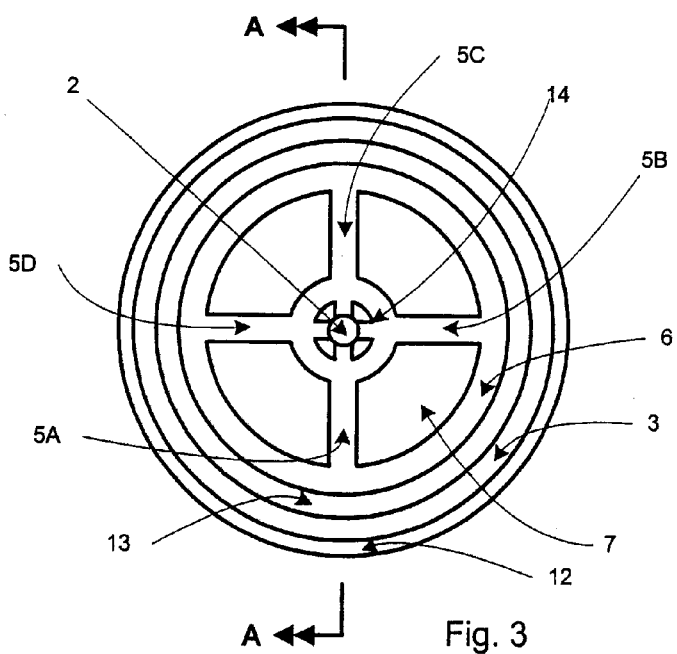
FIG. 3 is a schematic representation of the top of the scrubber cap.

FIG. 3 shows a plan view of the top of scrubber cap 1. Orifice 2 is connected by orifice bevel section 14 to four radial channels, identified as 5A, 5B, 5C, and 5D. Each of the radial channel 5A, 5B, 5C and 5D terminates at annular channel 6, so that annular channel 6 is in gas communication with each of radial channels 5A, 5B, 5C and 5D which in turn are in gas communication with orifice bevel section 14 and orifice 2. Annular channel 6 is surrounded by inner ledge 13 and then upper rim 3. Outer ledge 12 is shown on the periphery of upper rim 3. Outer ledge 12 is not essential, but inner ledge 13 is important in embodiments of the invention in that a membrane (not shown, but described below) that is placed over the channels of plate 7 may be bonded to inner ledge 13. The plane of plate 7 and inner ledge 13 should be the same.

Figure 4:
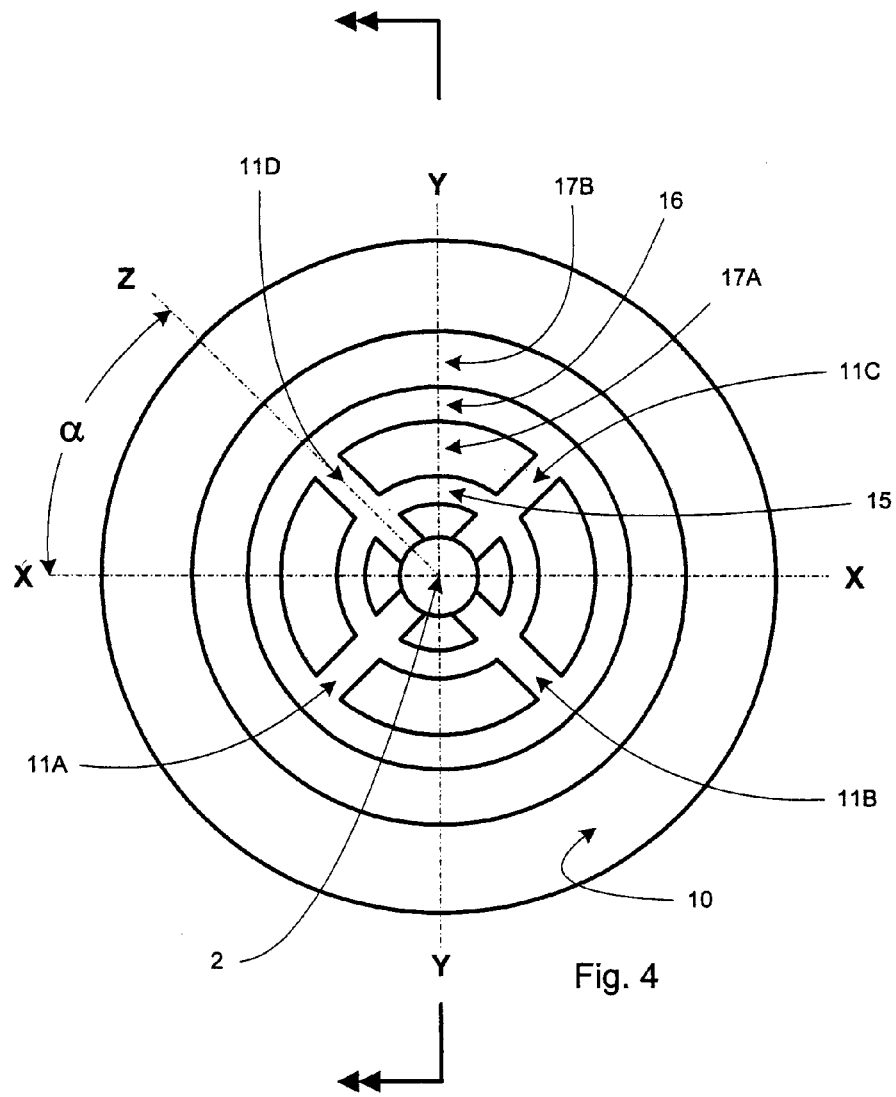
FIG. 4 is a schematic representation of the underside of the scrubber cap.

FIG. 4 shows a view of scrubber cap 1 from its underside. Orifice 2 is centrally located in the scrubber cap. Four radial channels, identified as 11A, 11B, 11C and 11D radiate from orifice 2. The orientation of the radial channels on the upper side of the scrubber cap is represented by X—X and Y—Y. The orientation of the radial channels on the underside of the scrubber cap is preferably as represented by the line Z, being at an angle to both X—X and Y—Y. The preferred angle is 45° when there are four radial channels, in view of the preferred symmetry of the radial channels. Thus, angle Δ shown in FIG. 4 is preferably 45° if there are four channels. Such an angle provides greater strength to plate 7, shown as plate 17A and 17B in FIG. 4, and consequently permits use of thinner plates as part of the scrubber cap. Radial channels 11A, 11B, 11C and 11D are shown as interconnecting with first under channel 15 and second under channel 16. Both of first under channel 15 and second under channel 16 are annular channels, being separated by section 17A of the plate, with section 17B of the plate being beyond second under channel 16. Lower rim 10 is shown as being a peripheral rim.

Figure 5:
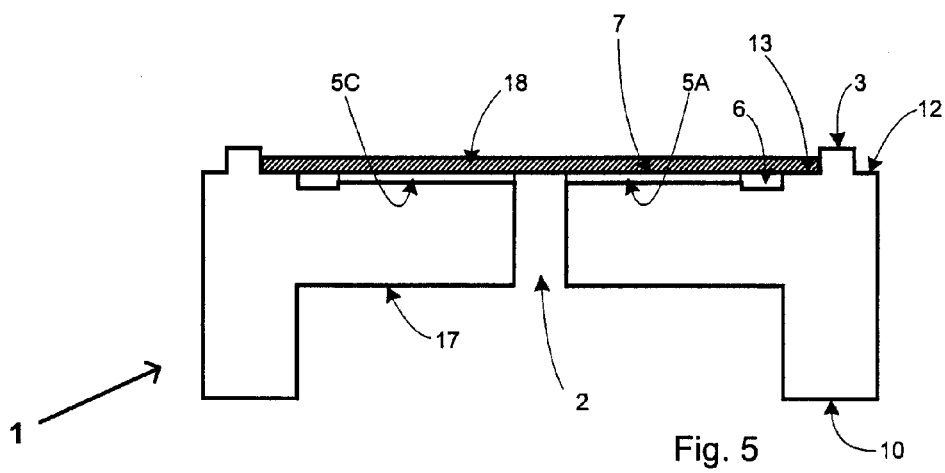
FIG. 5 is a schematic representation of the scrubber cap as viewed through A—A of FIG. 3.

FIG. 5 shows a cross section of the scrubber cap, through A—A of FIG. 3. Scrubber cap 1 has upper rim 3 and lower rim 10. Orifice 2 is centrally located within scrubber cap 1. Upper plate 7 extends away from orifice 2, forming radial channels 5A and 5C, which terminate in annular channel 6. In the embodiments shown in FIG. 5, there are no under channels, in contrast to FIG. 4. A membrane 18 is shown as extending across scrubber cap 1. Gas permeable membrane 18 rests on and is attached to inner ledge 13.

In operation, scrubber cap 1 with gas permeable membrane 18 attached thereto is placed on an electrochemical cell. The upper surface of membrane 18 as viewed in FIG. 5 is exposed to the atmosphere. At such time as a gas e.g. carbon monoxide, is present in the atmosphere, air and particularly carbon monoxide diffuses through membrane 18. The gas then diffuses around annular channel 6, to the extent required, along one or more of radial channels 5, to orifice 2. The gas then passes through orifice 2 into the region of the sensing electrode, not shown but located to the bottom of scrubber cap 1 as viewed in FIG. 5. In the event that one of the radial channels should become blocked for any reason, which is unlikely with membrane 18 in place, the gas may diffuse around annular channel 6 and pass along a different radial channel. It is more likely that a part of the surface of membrane 18 would become contaminated with a substance that retards the transmission of air and particularly carbon monoxide through the membrane. In that event, carbon monoxide could pass through a different part of the membrane and proceed around annular channel 6 to radial channels 5 and hence to orifice 2. The electrochemical sensor with a scrubber cap as described in place would continue to operate in an acceptable manner even though the upper surface of membrane 18 may have a substantial portion thereof coated with contaminant that retards a flow of gas through the membrane.

It is to be understood that there are two types of membrane that allow gases to go through. The first type is a gas porous membrane, in which the pores of the membrane should be small so that large particulate in the air can not enter the sensor. The second type is gas permeable membrane which has no pores. In this type of membrane, a gas must first dissolve in the membrane material, and then diffuse through the membrane to the other side to enter the sensor. Examples of the second type include TEFLON® film 50–200 LP PFA fluorocarbon manufactured by DuPont.

Figure 6:
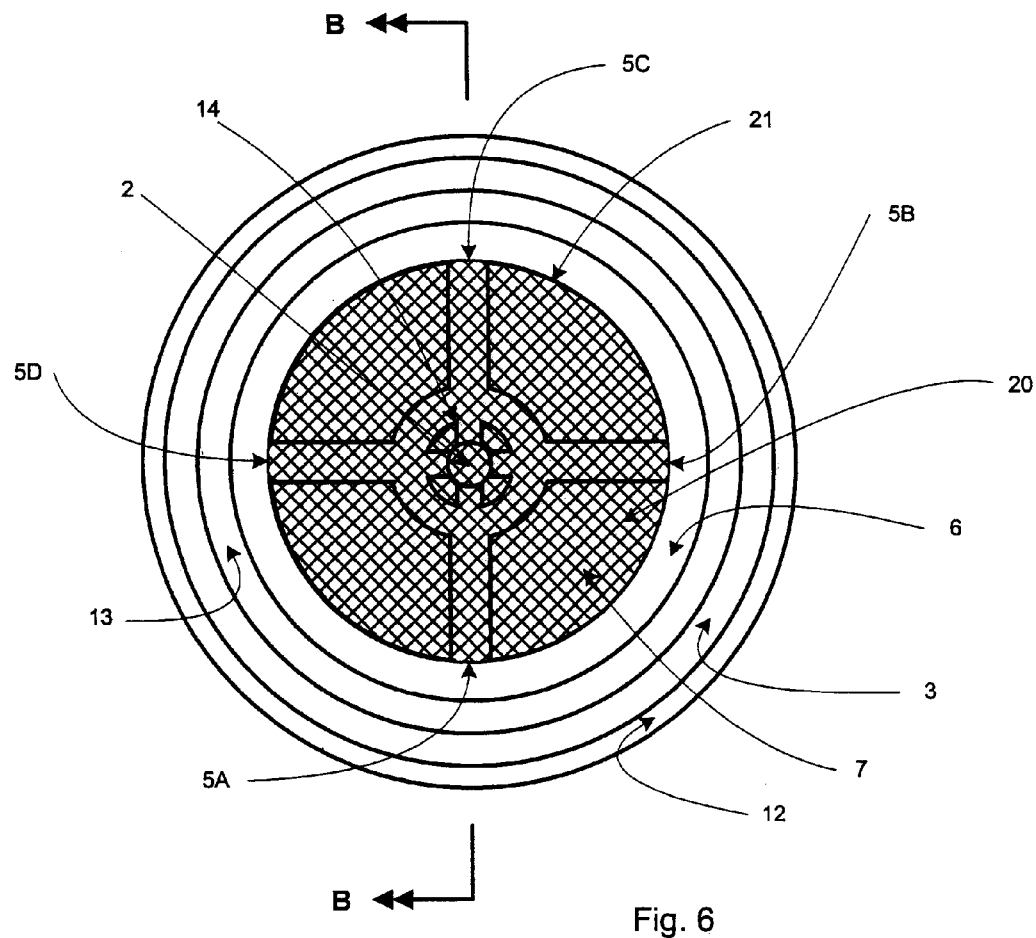
FIG. 6 is a schematic representation of another embodiment of the scrubber cap of FIG. 3.

FIG. 6 shows the scrubber cap as viewed in FIG. 3 but with alternate membrane 20. Alternate membrane 20 extends over orifice 2 and radial channels 5A–5D but terminates at the inner periphery 21 of annular channel 6. Alternate membrane 20 may be formed from a wide variety of hydrophobic materials, but it is preferred that alternate membrane 20 is not a gas permeable membrane, for economical reasons. In particular, alternate membrane 20 may be paper, polyethylene or other sheet or film material, coated or otherwise. In preferred embodiments, alternate membrane 20 has an adhesive e.g. a pressure-sensitive adhesive that will adhere to the material of the scrubber cap, so that alternate membrane 20 may be easily put into and retained in position.

Figure 7:
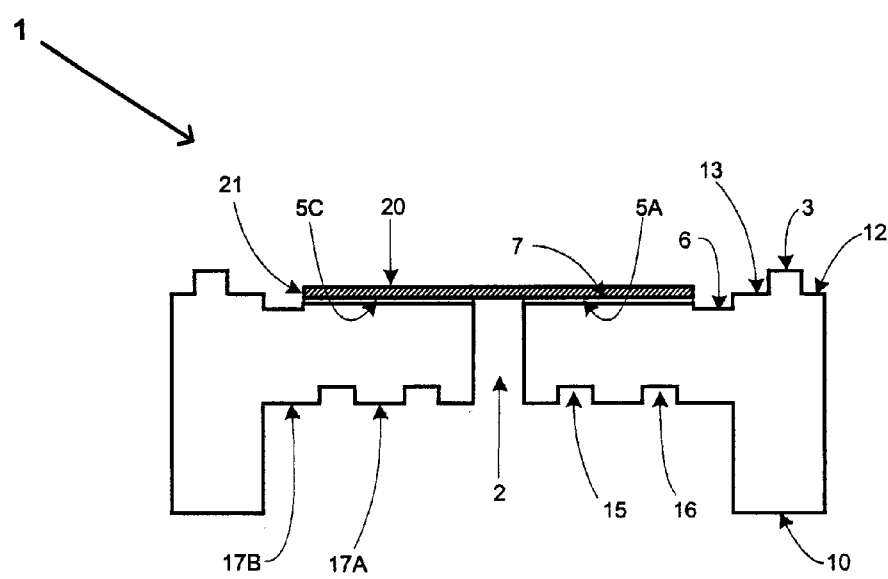
FIG. 7 is a schematic representation of the scrubber cap of FIG. 6, as viewed through B—B of FIG. 6.

The scrubber cap of FIG. 6 is shown in cross-section, through B—B, in FIG. 7.

Alternate membrane 20 provides protection against blockage or contamination of orifice 2. As illustrated in FIG. 6, annular channel 6 is open to the atmosphere. Gas from the atmosphere may pass from annular channel 6 through radial channels 5A–5D to orifice 2. If annular channel 6 should become partially blocked, the remainder of annular channel 6 remains open to the atmosphere. If one of the radial channels 5A–5D should be blocked, there would be in the embodiment shown three remaining radial channels open to the atmosphere.

FIG. 8 shows an alternate embodiment of the cross-section A—A of FIG. 3. In FIG. 8, radial channels 22 extend from orifice 2 on the underside of scrubber cap 1. Radial channels 22 terminate in annular channel 23. A gas porous membrane 24 extends over radial channels 22 and annular channel 23 in the same manner as described previous with respect to the upper side of scrubber cap 1. Gas porous membrane 24 contacts a layer of carbon pellets, 25, inside the electrochemical cell.

FIG. 8 particularly shows an embodiment in which carbon pellets are used in an electrochemical sensor for removal of contaminants e.g alcohol vapours, that could adversely affect the performance of the electrochemical cell, as is known. The embodiment of the invention shown in FIG. 8 provides protection against, in particular, partial or complete blockage of orifice 2 by particles of carbon while providing for flow of gas into the electrochemical cell. Use of radial channels 22 and common (annular) channel 23 provides for such flow. As discussed previously, there should be at least one radial channel, preferably two ore more radial channels disposed at an angle, and further disposed at an angle to any radial channels on the under side of the scrubber cap. Common channel 23 is preferably annular, but may be of any convenient shape, and as discussed above does not necessarily extend fully around the orifice.

The membranes used in the scrubber cap of the present invention are hydrophobic i.e. moisture resistant, or partly hydrophobic. Membranes that are not hydrophobic can be easily wetted, which could lead to the hole being blocked. Hydrophobic membranes also help prevent the channels from being flooded due to condensation of water.

The sensor housing is preferably made of a hydrophobic or partially hydrophobic material. It is particularly preferred that the surface of the scrubber cap be coated or pre-treated so as to be hydrophobic.

The present invention provides protection for an electrochemical sensor in operation, against contaminants, insects or other foreign bodies that could adversely affect flow of gas to be detected into the electrochemical cell.

What is claimed is:

1. An electrochemical sensor for detection of a gas in an atmosphere containing the gas, the sensor comprising
   (a) an electrochemical gas sensor cell with an electrolyte and at least two electrodes, one such electrode being a gas sassing electrode, and
   (b) a housing for the sensor cell and having an orifice and an open-faced radial channel connected in fluid flow communication to, and extending radially from, the orifice, the channel being on the outside surface of the housing such that gas in the atmosphere outside the housing travels through the orifice via the radial channel;
   the sensor cell being located in the housing such that the gas sensing electrode is in direct fluid communication with the orifice.

2. The electrochemical sensor of claim 1 in which there are at least two radial channels.

3. The electrochemical sensor of claim 2 in which the orifice is covered to prevent direct transmission of gas into the orifice.

4. The electrochemical cell of claim 3 in which each radial channel is fluidly connected to a common open-faced channel on the outside surface of the housing.

5. The electrochemical sensor of claim 4 in which the common channel is an annular channel around the orifice.

6. The electrochemical sensor of claim 4 in which the orifice is connected to at least three radial channels.

7. The electrochemical sensor of claim 6 in which the orifice is connected to at least four radial channels, each of the radial channels connecting with the common channel.

8. The electrochemical sensor of claim 7 in which there are four radial channels.

9. The electrochemical sensor of claim 4 in which the orifice and optionally the radial channels are covered by a hydrophobic film with low gas transmission characteristics, with gas transmission to the orifice being through said common channel and radial channels.

10. The electrochemical sensor of claim 4 in which the radial channels are disposed symmetrically about the orifice.

11. The electrochemical sensor of claim 4 in which the radial channels and any of the common channels are disposed on the outside surface of the housing, the inside surface of the housing, or on both surfaces of the housing.

12. The electrochemical sensor of claim 4 in which the said channels have a hydrophobic surface or a partly hydrophobic surface.

13. The electrochemical sensor of claim 4 in which the orifice and said channels are located in a scrubber cap, said scrubber cap being separable from said housing.

14. The electrochemical sensor of claim 4 in which the orifice and the radial and common channels are covered by a hydrophobic membrane.

15. An electrochemical sensor for detection of a gas in an atmosphere containing the gas, the sensor comprising
   (a) a housing having
      i. an orifice;
      ii. a plurality of open-faced radial channels connected in fluid flow communication to, and extending radially from, the orifice,
      iii. an open-faced annular channel around the orifice and fluidly connected to the radial channels, the radial and annular channels being on the outside surface of the housing such that gas in the atmosphere outside the housing travels through the orifice via at least one of the radial and annular channels;
   (b) a low gas transmission hydrophobic film on the outside surface of the housing covering the orifice and the radial and annular channels; and
   (c) an electrochemical gas sensor cell with an electrolyte and at least two electrodes, one such electrode being a gas sensing electrode; the sensor cell being located in the housing such that the gas sensing electrode is in direct fluid communication with the orifice.

* * * * *